US012636334B2

(12) United States Patent
Hammami et al.

(10) Patent No.: US 12,636,334 B2
(45) Date of Patent: **\*May 26, 2026**

(54) FOAM TREATMENT METHOD FOR BACTERIA

(71) Applicant: Imam Abdulrahman Bin Faisal University, Dammam (SA)

(72) Inventors: Ines Mohsen Hammami, Dammam (SA); Azzah Ibrahim Alghamdi, Dammam (SA)

(73) Assignee: Imam Abdulrahman Bin Faisal University, Dammam (SA)

( \* ) Notice: Subject to any disclaimer, the term of this patent is extended or adjusted under 35 U.S.C. 154(b) by 251 days.

This patent is subject to a terminal disclaimer.

(21) Appl. No.: 18/399,875

(22) Filed: Dec. 29, 2023

(65) Prior Publication Data

US 2024/0131102 A1 Apr. 25, 2024

Related U.S. Application Data

(63) Continuation of application No. 17/503,751, filed on Oct. 18, 2021, now Pat. No. 11,877,987, which is a continuation of application No. 16/149,674, filed on Oct. 2, 2018, now Pat. No. 11,191,800.

(51) Int. Cl.
*A61K 36/31* (2006.01)
*A61P 31/04* (2006.01)
(52) U.S. Cl.
CPC .............. *A61K 36/31* (2013.01); *A61P 31/04* (2018.01)
(58) Field of Classification Search
None
See application file for complete search history.

(56) References Cited

U.S. PATENT DOCUMENTS 11,191,800 B2 \* 12/2021 Hammami .............. A61P 31/04
11,877,987 B2 \* 1/2024 Hammami .............. A61P 31/04

2008/0044497 A1 2/2008 Sussan
2008/0182751 A1 7/2008 Morra et al.
2019/0262255 A1 8/2019 Stein

FOREIGN PATENT DOCUMENTS

FR 2 950 250 A1 3/2011
WO 1993/005153 A1 3/1993
WO 2006/136933 A2 12/2006
WO 2011/099878 A2 8/2011

OTHER PUBLICATIONS

Koubaa, et al. ; Antioxidant and antimicrobial activities of solvent extract obtained from rocket (*Eruca sativa* L.) flowers ; Free Radicals and Antioxidants, vol. 5, Issue 1 ; Jan.-Jun. 2015 ; 6 pages.
Alaridh, et al. ; Evaluation of Green Synthesis of Ag Nanoparticles Using Eruca sativa and Spinacia oleracea Leaf Extracts and Their Antimicrobial Activity ; Iran J Biotech 12 (1) ; Mar. 2014 ; 6 pages.
Prasad ; Antimicrobial potential of Brassicaceae family against clinical isolates ; International Journal of Pure & Applied Bioscience ; 2 (2) ; pp. 158-162 ; 2014 ; 5 pages.
Ali et al. Baghdad Science Journal 4(3):375-378 , Sep. 2007, abstract.

\* cited by examiner

*Primary Examiner* — Brian J Davis

(74) *Attorney, Agent, or Firm* — Oblon, McClelland, Maier & Neustadt, L.L.P.

(57) ABSTRACT

The invention is directed to an aqueous extract of *Eruca sativa* (arugula) leaves that has antimicrobial activity on Gram-positive bacteria and mycoplasmas. The extract may be purified away from solid or insoluble components, standardized based on the weight of its non-aqueous or solid content, assayed for antimicrobial activity, and provided in an aseptic or sterile form for pharmaceutical use. It may be used to kill or inhibit the growth of microorganisms such as Gram positive bacteria, promote wound healing, or as prophylaxis against host colonization or infection by a microorganism.

7 Claims, 2 Drawing Sheets

FOAM TREATMENT METHOD FOR BACTERIA

CROSS-REFERENCE TO RELATED APPLICATIONS

The present application is a Continuation of U.S. application Ser. No. 17/503,751, now allowed, having a filing date of Oct. 18, 2021 which is a Continuation of U.S. application Ser. No. 16/149,674, now U.S. Pat. No. 11,191, 800, having a filing date of Oct. 2, 2018.

BACKGROUND OF THE INVENTION

Field of the Invention. The invention falls within the fields of biochemistry and microbiology. It pertains to an aqueous extract of leaves of *Eruca sativa* sometimes known as arugula that can be used to inhibit the growth of Gram-positive bacteria such as those that contaminate skin wounds and lesions. *Eruca sativa* is an edible plant within the Brassicaceae family.

Description of Related Art. This "background" description provides a general context helpful in understanding the invention. The work of the presently named inventor(s) to the extent that it is described in this section, as well as aspects of the description which may not otherwise qualify as prior art at the time of filing, are neither expressly or impliedly admitted as prior art against the present invention.

Plant extracts have been used in traditional medicine since ancient times to treat or eliminate disease. Building on this foundation of traditional medicine, an impressive number of drugs have been isolated from plant sources for treatment of human, animal and plant diseases. The new herbal extracts and drugs derived from them are used to treat diseases or infestations caused by viruses, bacterial, fungi, parasites and insects. Modern biochemists, microbiologists and physicians continue the quest to discover new plant extracts and components useful in agronomy, animal science and medicine.

Phytochemicals and extracts from the Brassicaceae family contribute beneficial components to the human diet and are being studied to determine whether they contain other biologically beneficial components. WO2006136933A2 and WO1993005153A1 involve evaluation of extracts of Brassicaceae seeds for use as a pesticide or as an antifungal or antibacterial agent. US 2008/0182751 A1 evaluated processed plant material from Brassicaceae for use against plant pests. WO2011099878A2 evaluated antimicrobial effects of a fermented concoction of tropical plants including those of Brassicaceae. FR2950250A1 describes organic solvent extracts of Brassicaceae. Koubaa, et al., Free Radicals and Antioxidants 5(10): 29-34 (2015) evaluated the antibacterial activity of non-polar compounds extracted by hexane from *Eruca sativa* flowers. Alaraidh, el al., Iran J. Biotech, 12(1) (2014) describes antimicrobial silver nanoparticles produced using *Eruca sativa* leaf extracts. Prasad, Int. J. Pure and Appl. Biosci. 2(2):158-162 (2014) evaluated antimicrobial properties of organic solvent extracts of plants in the *Brassica oleracea* family. Despite much interest and ongoing research, much is still not known about which plants, or plant extracts, contain beneficial components.

In view of the emerging antibiotic resistance of many Gram positive bacteria, such as methicillin-resistant *staphylococcus* (MRSA), there is a significant need and demand for new antimicrobial drugs and agents especially those derived from non-toxic natural components such as *Eruca sativa*.

With this objective in mind the inventors diligently sought to identify fractions and components of *Eruca sativa* that exhibit antimicrobial activity.

BRIEF DESCRIPTION OF THE INVENTION

An object of the invention is to provide therapeutic or antimicrobial compositions obtained from aqueous extraction of *Eruca sativa* leaves and methods for extracting and purifying these compositions. Advantageously, in some embodiments the leaf extract can be purified away from solid or insoluble components of *Eruca sativa*, standardized based on the weight of its anhydrous or solid content, assayed for antimicrobial activity, and provided in an aseptic or sterile form for therapeutic use.

A further object of the invention is to provide methods for treating infections caused by Gram-positive bacteria and mycoplasmas using these therapeutic compositions.

An additional object of the invention is to provide methods for promoting wound healing using these therapeutic compositions.

A further object of the invention is to provide methods for preventing the growth or colonization of a subject or object with Gram-positive bacteria or mycoplasmas using antimicrobial compositions of the invention.

These and other objects of the invention will become evident from this disclosure.

DETAILED DESCRIPTION OF THE INVENTION

Figure 1A:
FIGS. 1A and 1B depict *Eruca sativa* and its leaves.
Figure 1B:

The invention generally pertains to an aqueous extract of the leaves of *Eruca sativa*, compositions incorporating this extract, and methods for using this extract to inhibit the growth of Gram-positive bacteria, *mycoplasma* and other microorganisms, or as prophylaxis against infection or colonization of a host or object with such microorganisms.

Compositions containing these extracts can be administered to treat or promote the healing of injuries including those to the skin, hair and nails (including pimples, acne, and sites of dermatitis, and dermal damage associated with aging), to mucous membranes such as those to the eyes, the nasal and oral cavities, urinary tract, reproductive organs, GI tract, or to other tissues susceptible to microbial colonization or infection.

The invention is described by reference to the following definitions and features. Various embodiments of the invention may incorporate one or more features, elements, ranges or alternatives described below.

An "*Eruca sativa*" extract contains one or more components besides water aqueously extracted from the leaves of *Eruca sativa*, sometimes known as arugula, rocket salad, rucuola, rucoli, rugla, colewort or roquette. In some embodiments, the extract is made from fresh leaves, in others from dried, frozen or otherwise preserved leaves.

An aqueous extract is prepared by mashing, macerating, blending, sonicating, freeze-thawing, French pressing, digesting, or otherwise disrupting *Eruca sativa* leaves so that water-soluble components can be removed and recovered. Generally extraction is performed in an aqueous or water-based solution which may contain salt(s), buffers, stabilizers, enzymes, chelators (e.g., of divalent cations or metals like iron), antioxidants and/or preservatives. In some embodiments water-soluble components from *Eruca sativa* leaves are extracted using non-water polar solvents or solvents that are miscible with water, or mixtures of these solvents with water.

A solution for aqueous extraction of leaves will contain sufficient water or other aqueous solvent to extract components of *Eruca sativa* that are soluble in water. Such a solvent may contain 0 to 100 wt % water or any endpoint or intermediate value within this range, for example, 100, 95, 90, 80, 75, 70, 65, 60, 55, 50, 45, 40, 35, 30, 25, 20, 15, 10, or 5 wt % water. The extraction may be made using a single aqueous phase or may be made using a multiple phase extraction, such as with an aqueous solvent in combination with one or more immiscible phases; e.g., an extraction in which hydrophilic solutes go into an aqueous phase and hydrophobic solutes go into a hydrophobic phase.

In some embodiments water-soluble components of *Eruca sativa* leaves are extracted by steam, water vapor or another gaseous or vaporous hydrophil or polar solvent.

Polar solvents include those having a dielectric constant of at least 15, 20, 30, 40, 50, 60, 70, 80 or more or any intermediate value within this range. Examples of polar solvents include water, methanol, ethanol, n-propanol, isopropanol, DMSO, and mixtures thereof.

In other embodiments extraction may be performed under acidic, neutral or alkaline conditions ranging from pH 1.0 to pH 14.0 and all intermediate subranges and values. These include extraction at a pH of 2.0, 2.5, 3.0, 3.5, 4.0, 4.5, 5.0, 5.5, 6.0, 6.5, 7.0, 7.5, 8.0, 8.5 or 9.0. In one embodiment, extraction is performed at a pH ranging from 6.0 to 8.0.

In some embodiments, extraction times range from ≤5, 10, 15, 30, or 60 minutes, or 1, 2, 3, 4, 5, 6, 7, 8, 9, 10, 11, 12, 15, 18, 20, 24 or more hours.

To facilitate the extraction of soluble components surfactants, chelators, and/or enzymes that digest *Eruca sativa* leaves, such as cellulase (e.g., endo-1,4-beta-D-glucanase (beta-1,4-glucanase, beta-1,4-endoglucan hydrolase, endoglucanase D, 1,4-(1,3,1,4)-beta-D-glucan 4-glucanohydrolase), carboxymethyl cellulase (CMCase), avicelase, cellu-dextrinase, cellulase A, cellulosin AP, alkali cellulase, cellulase A 3, 9.5 cellulase, and pancellase SS), proteases (e.g., serine-, cysteine-, threonine-, aspartic-, glutamic-, or metallo-proteases, and asparagine peptide lyases), or nucleases (RNAase, DNAase), may be used.

Extraction may be performed at different temperatures, for example, from 0, 5, 10, 15, 20, 25, 30, 35, 40, 45, 50, 55, 60, 65, 70, 75, 80, 85, 90, 95, or 100° C. (or at higher temperatures under pressure) or any intermediate temperature within this range.

An *Eruca sativa* leaf extract can be further purified by removing insoluble or solid components from an aqueous extract, for example, by separating these solid components from liquid components by centrifugation or filtration. Protein and non-protein components may be separated or isolated from one another by filtration, precipitation, chromatography or by addition of a protease.

Proteins may be isolated by the chromatographic procedures described herein or by precipitation, and/or differential solubilization.

Oils and hydrophobic components removed by aqueous extraction may be separated from aqueous components by phase partition based on their differential solubility in non-aqueous solvents, such as a solvent having a dielectric constant of less than 15, 10, 5, or 2. Nonpolar solvents include chloroform, diethylether, hexanes, benzene and toluene An extract can be dialyzed to remove salts or other cations and anions or other low molecular weight solutes. Dialysis membranes having molecular weight cutoffs ranging from 1, 5, 10, 50, 100, 500, 1,000, 5,000, 10,000, 50,000, 100,000, 500,000 or 1,000,000 kDa or any endpoint or intermediate cutoff value within this range may be employed for this purpose.

A dialysis buffer can be selected to effect solvent exchange in an extract, for example, to alter the ionic concentration or pH of an extract.

One skilled in the art can select an appropriate dialysis buffer, temperature, and duration, for example, dialysis may be performed at 4° C. or at 25'C for 2, 4, 6, 8, 10, 12, 18, or 24 hours. Dialysis buffer may be replaced and dialysis repeated 1, 2 or more times if desired.

An aqueous extract may be further purified chromatographically. For example, an aqueous extract may be fractionated by size exclusion chromatography, affinity chromatography, HPLC, hydrophobic interaction chromatography, ion-exchange chromatography or free-flow electrophoresis by methods known to those skilled in the art.

An *Eruca sativa* extract may be further treated to render it stable, aseptic or sterile. Such methods include but are not limited to filtration, heat pasteurization or sterilization, addition of chelators such as EDTA, EGTA, vitamin C or other antioxidants, or oxidants such as hydrogen peroxide. Microbial contaminants may be removed by filtration, for example, through a 0.1, 0.2, 0.22, or 0.45 micron filter. A fresh extract may be refrigerated, frozen, or lyophilized for storage.

A purified *Eruca sativa* aqueous extract, preferably one having the solid leaf components removed, can be concentrated by removing a portion of or all of the aqueous solvent. A concentrated aqueous extract will have a lower concentration of water and higher relative concentration of water-soluble components from *Eruca sativa* than an original or starting extract. A concentrated extract may contain 1, 5, 10, 20, 30, 40, 50, 60, 70, 80, 90, 95 or <100 wt % of water or the aqueous solvent contained in the original leaf extract. This range includes any intermediate value.

An anhydrous, dry or desiccated *Eruca sativa* extract will have substantially all of the aqueous solvent removed from it.

Concentration and dehydration methods are known in the art and include, but are not limited to, those performed with a device such as hot air blower, dryer, cylindrical dryer, zeolite dryer, a desiccator, or a freeze-dryer. An extract can be concentrated or dried by evaporating the solvent using a falling film device, low pressure evaporator, or spray tower.

A fresh, concentrated, or dried extract may be stored under sterile or aseptic conditions that prevent loss of its antimicrobial activity, for example, it may be stored in liquid nitrogen, or at −86° C., −70° C., −20° C., 4° C. or stored in desiccated form in sealed ampules.

*Eruca sativa* compositions. The term "composition" includes those with one or more ingredients. Thus, an original aqueous extract of *Eruca sativa* without further additions is a composition. A composition may contain fewer ingredients than those present in an original aqueous extract provided that a therapeutic or antimicrobial activity is retained. For example, it can omit water or salts present in an original aqueous extract or consist of the anhydrous components of a leaf extract.

In some embodiments, a composition will contain one or more ingredients, one or more combinations of ingredients, or a greater content of an ingredient, than those or that present in the original aqueous extract. For example, it may contain a preservative, antioxidant, chelator, or a pharmaceutically acceptable carrier or excipient not present in an original *Eruca sativa* aqueous extract or may be a combination of an *Eruca sativa* extract and an aqueous or nonaqueous extract of another plant.

A composition may contain 0.1, 0.2, 0.5, 1.0, 2.0, 3.0, 4.0, 5.0, 6.0, 7.0, 8.0, 9.0, 10, 15, 20, 25, 30, 35, 40, 45, 50, 55, 60, 65, 70, 75, 80, 85, 90, 95, 99 or 100 wt % (or any endpoint or intermediate value within this range) of an *Eruca sativa* extract, for example, it may contain 1 wt % of an anhydrous *Eruca sativa* extract and 99 wt % water or other carrier or excipient. Preferably, it will contain a therapeutically effective amount of the extract. By an "effective" amount or a "therapeutically effective" amount of the *Eruca sativa* extract is meant a nontoxic but sufficient amount of the agent to provide a beneficial effect. The amount of active agent that is "effective" will vary from subject to subject, depending on the age and general condition of the individual, the particular active agent or agents, and the like. Unless otherwise indicated, the term "therapeutically effective" amount as used herein is intended to encompass an amount effective for the prevention, the amelioration of an adverse condition and/or treatment of the adverse condition. Determination of a therapeutic effect may be made by comparison with an otherwise identical composition that does not contain the *Eruca sativa* extract, or which contains a control extract from a different plant.

The terms "treating" and "treatment" as used herein refer to the administration of a composition containing an *Eruca sativa* extract to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. Analogously, this term also applies to treatment of objects, such as contacting an extract with a surface or surgical equipment to kill, inhibit or remove microbial contaminants.

The terms "preventing" and "prevention" refer to the administration of an agent or composition to a clinically asymptomatic individual who is susceptible to a particular adverse condition, disorder, or disease, and thus relates to the prevention of the occurrence of symptoms and/or their underlying cause. For example, treatment may decrease in the number of Gram-positive bacteria in a wound, reduce inflammation, accelerate wound healing, or prevent or ameliorate scar formation. Analogously, this term also applies to prevention of bacterial contamination of objects, such as contacting an extract with a surface or surgical equipment to prevent or remove microbial contamination.

Therapeutic Compositions. A composition may be formulated for therapeutic use, for example, with a pharmaceutically acceptable excipient or excipient in aseptic or sterile form. It may also include other therapeutically active ingredients, such as anesthetics, plant extracts, antibiotics, or other antimicrobial agents.

In some embodiments, the composition of the invention will incorporate one or more non-*Eruca sativa* antimicrobial or antiviral herbal extracts. Such herbs include *Calendula officinalis, Cinnamomum zeylanicum, Syzygium aromaticum, Allium sativum, Echinacea anguslifolia, Mahonia aquifolium, Althaea officinalis* L.), *Usnea barbata, Arctostaphylos uva-ursi, Achillea millefolium, Astragalus membranaceus, Uncaria lomenlosa, Vaccinium macrocarpon, Sambucus nigra, Zingiber officinale, Melissa officinalis, Glycyrrhiza glabra, Verbascum Thapsus, Olea europaea,* and/or *Origanum vulgare.* These herbal extracts include the oil and oily or dry components of these herbs as well as their aqueous components. An appropriate content of *Eruca sativa* and one or more other herbal extracts may be selected based on maximizing the antimicrobial activity of the mixtures. In some embodiments the ratio of *Eruca sativa* aqueous extract to another herbal extract will range from 0.1 to 100 to 100 to 0.1 as well as any endpoint or intermediate ratio. Such ratios include 50:1, 20:1, 10:1, 5:1, 2:1, 1:1, 1:2, 1:5, 1:10, 1:20, and 1:50 and may be based on the weight on anhydrous or solid components of the extracts.

In other embodiments, extracts from cruciferous vegetables or chemical components of cruciferous vegetables may be added or incorporated into an *Eruca sativa* extract. Cruciferous vegetables act as good sources of natural compounds because of high levels of carotenoids, tocopherols, and ascorbic acid.

In some embodiments, an *Eruca sativa* extract may be supplemented with natural chemical compounds present in *Eruca sativa. E. sativa* has been recognized as a rich source of health-promoting phytochemicals, vitamins, carotenoids, fibers, minerals, glucosinolates, isothiocyanates, flavonoids such as kaempferol, quercetin, and isorhamnetin, flavanols, and phenolic compounds. Glucosinolates can be used to increase or confer anticarcinogenic, antifungal, antibacterial, and antioxidant activities on an extract. Addition of flavonoids may increase or confer additional anti-inflammatory, estrogenic, enzyme inhibition, antimicrobial, antiallergic, vascular, cytotoxic, antitumor, antioxidant, and free radical scavenging activities on an *Eruca sativa* extract.

The *Eruca sativa* leaf extract of the invention may also be formulated along with, or used or administered in conjunction with, traditional remedies prepared from alum, anise, arak, asafetida, banana, black seed (*Nigella sativa*), caraway, cardamom, chamomile, cucumber, frankincense, garlic, myrrh, nakhwa, petroleum (naft, batrul), pomegranate, saffron, thyme, turmeric, or walnut bark. Treatments and modes of administration are incorporated by reference to hypertext transfer protocol://archive.aramcoworld.com/issue/200605/natural.remedies.ofarabia.htm (last accessed Apr. 13, 2017). Plant extracts may be in the form of an aqueous, alcohol or other organic solvent, or oily extract, may be in dry or powdered form, or may contain purified active components from these traditional remedies.

In some embodiments a composition of the invention will contain an antimicrobial component such as those described by Capelli, U.S. Pat. No. 5,662,913, Kaiser, et al., U.S. Pat. No. 6,383,505 B1, Mansouri, U.S. Pat. No. 6,579,516, and Koller, et al., U.S. Pat. No. 8,980,243, each of which is incorporated by reference.

Advantageously a composition will contain a concentration of *Eruca sativa* extract and/or other active ingredients, sufficient to prevent or inhibit the growth of a target microorganism such as the Gram positive bacteria described herein. When a composition includes both the *Eruca sativa* extract and another active ingredient it may exhibit additive or synergistic therapeutic and/or antimicrobial activity, or the mixture of two active ingredients may expand its antimicrobial spectrum.

In some embodiments, the therapeutic or antimicrobial *Eruca sativa*-based compositions will be formulated for application to wounds in skin or mucous membranes, such as epidermal wounds or wounds in the eyes, nose or the mouth. For example, in the treatment of eye infections or other infections of mucous membranes, the composition, in the form of a solution, wash, lotion, emulsion, ointment or a cream, can be applied to the mucous membrane of the patient using standard techniques. Standard methods known in the medical and pharmaceutical arts are used to formulate and apply these compositions to wounds.

In the treatment of mouth infections, including gingivitis, the composition may be formulated as a solution or cream can be applied using a sponge applicator or a toothbrush. It may also be incorporated into a gargling solution, mouthwash or rinse.

The compositions of the invention may also be in the form of a solution and used for infusing into a body cavity (e.g., a surgical wash) and thereby treating or reducing the risk of infection or may be prepared in an inhalable or aerosol form for administration to the respiratory system.

In other embodiments, the composition is formulated as a wound dressing or bandage can that can provide sustained contact or release of an *Eruca sativa* extract with a wound and inhibit the growth of Gram-positive bacteria and other microorganisms while also preventing contamination or desiccation of a wound.

Formulations. A composition containing the *Eruca sativa* aqueous extract may be provided in various forms. Formulations may include other active ingredients and/or non-toxic, inert pharmaceutically suitable excipients such as solid, semisolid or liquid diluents, fillers, or adjuvants.

Formulations may be in solid, semisolid or viscous, liquid, aerosol or vaporous forms. They may have acidic or basic pHs and may contain water and/or organic ingredients such as alcohols and other conventional organic excipients, such as those used in pharmaceutical or cosmetic products. A formulation may be in the form of a solution, tincture, wash (e.g., surgical or dental washes), foam, spray, serum, gel, suppository, suspension, emulsion, cream, lotion, paste, ointment, granule, powder, freeze-dried or desiccated form, troche, capsule, tablet, or pill. An antiseptic or cleaning formulation may contain ingredients conventionally included in such products such as water, organic compounds, chelators, surfactants, oxidants and disinfectants. The particular formulations described in detail below may contain chelators or antioxidants as well as other conventional excipients or carriers.

Chelator. Compositions according to the invention may incorporate one or more chelators that can sequester elements like calcium or iron necessary for bacterial growth. Examples of chelators of iron and calcium include, but are not limited to, diethylene triamine pentaacetic acid (DTPA), ethylene diamine tetraacetic acid (EDTA), nitrilotriacetic acid (NTA), 1,3-propylene diamine tetraacetic acid (PDTA), Ethylene diamine disuccinic acid (EDDS), and ethylene glycol tetrancetic acid (EGTA). Any suitable chelating agent known in the art, which is biologically safe and able to chelate iron, calcium or other metals, is suitable for the invention. Suitable biocompatible chelating agents useful in conjunction with the present invention include, without limitation, monomeric polyacids such as EDTA, cyclohexanediamine tetraacetic acid (CDTA), hydroxyethylethylenediamine triacetic acid (HEDTA), diethylenetriamine pentaacetic acid (DTPA), dimercaptopropane sulfonic acid (DMPS), dimercaptosuccinic acid (DMSA), aminotrimethylene phosphonic acid (ATPA), citric acid, pharmaceutically acceptable salts thereof, and combinations of any of the foregoing. Other exemplary chelating agents include: phosphates, e.g., pyrophosphates, tripolyphosphates, and hexametaphosphates. Such chelators may be incorporated in amounts sufficient to bind to the divalent cations or metals, such as iron, in a composition or in a wound to which the composition is applied. For example, the concentration may be selected to bind to at least 25, 50, 75 or 100 mole % of the calcium, magnesium, or iron in a composition or wound.

Antioxidants. Antioxidants suitable for use in pharmaceutical, cosmetic, and food products are known. BHT (butylated hydroxytoluene) and BHA (butylated hydroxyanisole) are two common oil soluble antioxidants. Tocopherols (Vitamin E derivatives, e.g., alpha-tocopherol) and ascorbyl palmitate may also be used. Ascorbates, such as vitamin C, and propyl gallate are examples of water soluble antioxidants. Alpha lipoic acid, acetyl carnitine, Coenzyme Q10 (ubiquinol), selenium, retinoic acid, B vitamins, flavonoids, and various algae and plant extracts may also be used as antioxidants. Such antioxidants can be incorporated in amounts sufficient to quench free radicals in a composition or in a wound to which the composition is applied. For example, the concentration may be selected to bind to at least 25, 50, 75 or 100 mole % of the free radicals in a composition or wound.

Other Ingredients and Excipients. In addition to the active ingredient(s), the formulations described herein, depending on their particular physical and chemical formulation may contain the customary excipients, for example animal and vegetable fats, waxes, paraffins, starch, tragant or cellulose derivatives, polyethylene glycols, silicones, bentonites, silicic acid, talcum, and zinc oxide, or mixtures of these substances.

Aqueous suspensions may contain customary excipients such as liquid diluents, for example water, ethyl alcohol, propylene glycol, suspending agents, for example ethoxylated isostearyl alcohols, polyoxyethylene sorbit and sorbitan esters, microcrystalline cellulose, aluminum metahydroxide, bentonite, agar-agar and tragant, or mixtures of these substances.

The kinds of formulations mentioned herein may also contain colorants, preservatives and odor- and flavor-enhancing additives, for example peppermint oil and eucalyptus oil, and, for ingestible products sweeteners and flavorings. Solutions and emulsions according to the invention may contain the customary excipients such as solvents, solubilizers and emulsifiers, for example water, ethyl alcohol, isopropyl alcohol, ethyl carbonate, ethyl acetate, benzyl alcohol, benzyl benzoate, propylene glycol, 1,3-butylene glycol, dimethyl formamide, oils, in particular cottonseed oil, peanut oil, corn oil, olive oil, castor oil and sesame oil, glycerin, glycerol formal, tetrahydrofurfuryl alcohol, polyethylene glycols and fatty acid esters of sorbitan, or mixtures of these substances.

Some specific kinds of formulations of compositions containing an aqueous extract of *Eruca sativa* are described below.

Topical formulations. Topical formulations include antimicrobial pharmaceuticals, deodorants, soaps, body washes, shampoos, lubricants (e.g., for catheters or other devices, anatomical sites, or surfaces at risk of microbial contamination), hand or skin sanitizers and disinfectants and personal care products (e.g., a product that is used for personal hygiene). A topical formulation can be provided in a variety of formulations including but not limited to solutions, tinctures, gels, serums, creams, colloids, emulsions, lotions, solid sticks, aerosols or dry powders as described in U.S. Pat. Nos. 4,844,902; 6,818,226; 6,469,015; 7,147,854; 7,192,607; 7,205,003; and 7,252,831, each of which is hereby incorporated by reference in its entirety.

Aqueous solutions. The *Eruca sativa* extract of the invention may be dissolved in water, another solvent miscible with water, or a mixture thereof. It may contain other solutes or liquid components such as salts, chelators (e.g., EDTA, EGTA), antioxidants, or preservatives. In some embodiments it may further comprise an acid, a base, or buffer for adjusting or stabilizing the pH of an aqueous composition so as to maintain or maximize antibacterial activity of the *Eruca sativa* extract or for suitability for treatment of a particular type of wound. For example, the acid or base is useful for adjusting the pH of the present aqueous compositions to a pH of about 1 to about 14 (e.g., from about 1 to about 2, from about 2 to about 2, from about 3 to about 4, from about 4 to about 5, from about 5 to about 6, from about 6 to about 7, from about 7 to about 8, from about 8 to about 9, from about 9 to about 10, from about 10 to about 11, from about 11 to about 12, from about 12 to about 13, from about 13 to about 14, or any other value or range of values therein). In certain embodiments, the pH of the present aqueous composition ranges from about 3.5 to about 13; in other embodiments, from about 6.5 to about 8.5. In some embodiments, the pH is about 13; in other embodiments, the pH is about 7.5 to about 8.4. In certain embodiments, the pH of the present aqueous composition ranges from about 5 to about 13; from about 6 to about 13; from about 7 to about 13; from about 8 to about 13; from about 9 to about 13; from about 10 to about 13; from about 11 to about 13; from about 12 to about 13. Such pH adjustment can improve the dispersibility of ingredients present in an aqueous composition.

Acids useful in the present aqueous compositions include inorganic acids such as carbonic acid, sulfuric acid, or hydrochloric acid. Organic acids can alternatively be employed. Suitable organic acids include $C_1$ to $C_{20}$ organic acids such as formic acid, citric acid, malic acid, adipic acid, tannic acid, lactic acid, ascorbic acid, acetic acid, fumaric acid, and mixtures thereof. In one embodiment, the acid is citric acid. In some embodiments, the aqueous compositions do not comprise an acid. These ranges include all intermediate values as well as endpoints.

Bases useful in the present aqueous compositions may be organic or inorganic bases. Suitable inorganic bases include alkali metal or alkaline earth metal compounds such as sodium hydroxide, lithium hydroxide, potassium hydroxide, sodium carbonate, potassium carbonate, sodium bicarbonate, potassium bicarbonate, magnesium carbonate and calcium carbonate. Other suitable bases include ammonium hydroxide, substituted amine bases and ammonia. In some embodiments, the aqueous compositions do not comprise a base. These ranges include all intermediate values as well as endpoints.

In other embodiments, the aqueous compositions can comprise one or more salts. Salts useful in the present aqueous compositions include organic or inorganic salts. Suitable salts include alkali or alkaline earth metal salts such as sodium chloride, sodium nitrate, potassium chloride, calcium chloride, magnesium chloride, ammonium chloride, sodium bromide, potassium bromide, calcium bromide, magnesium bromide, ammonium bromide, sodium iodide, potassium iodide, calcium iodide, magnesium iodide, ammonium iodide, sodium sulfate, potassium sulfate, calcium sulfate, magnesium sulfate, ammonium sulfate. The salt can present in the aqueous compositions in an amount from 0 wt % to about 30 wt % (e.g., 0 to about 0.5 wt %, about 0.5 wt % to about 1 wt %, about 1 wt % to about 2 wt %, about 2 wt % to about 3 wt %, about 3 wt % to about 4 wt %, about 4 wt % to about 5 wt %, about 5 wt % to about 6 wt %, about 6 wt % to about 7 wt %, about 7 wt % to about 8 wt %, about 8 wt % to about 9 wt %, about 9 wt % to about 10 wt %, about 10 wt % to about 11 wt %, about 11 wt % to about 12 wt %, about 12 wt % to about 13 wt %, about 13 wt % to about 14 wt %, about 14 wt % to about 15 wt %, about 15 wt % to about 16 wt %, about 16 wt % to about 17 wt %, about 17 wt % to about 18 wt %, about 18 wt % to about 19 wt %, about 19 wt % to about 20 wt %, about 20 wt % to about 21 wt %, about 21 wt % to about 22 wt %, about 22 wt % to about 23 wt %, about 23 wt % to about 24 wt %, about 24 wt % to about 25 wt %, about 25 wt % to about 26 wt %, about 26 wt % to about 27 wt %, about 27 wt % to about 28 wt %, about 28 wt % to about 29 wt %, about 29 wt % to about 30 wt %, or any other value or range of values therein) of the aqueous composition. In some embodiments, the salt is present from about 0.01 wt % to about 0.05 wt % of the aqueous compositions. In some embodiments, the aqueous compositions do not contain a salt.

In other embodiments the aqueous compositions contain water or solvents miscible with water or a mixture of both. An aqueous composition may contain an amount of *Eruca sativa* extract that exhibits antimicrobial or therapeutic (e.g., wound healing, etc.) activity in combination with an amount of solvent sufficient to keep the extract in solution or to dissolve a dry extract. In some embodiments, the amount of water or aqueous solvent in the present aqueous compositions can range from about 10 to about 90 wt % (e.g., about 10 wt % to about 15 wt %, about 15 wt % to about 20 wt %, about 20 wt % to about 25 wt %, about 25 wt % to about 30 wt %, about 30 wt % to about 35 wt %, about 35 wt % to about 40 wt %, about 40 wt % to about 45 wt %, about 45 wt % to about 50 wt %, about 50 wt % to about 55 wt %, about 55 wt % to about 60 wt %, about 60 wt % to about 65 wt %, about 65 wt % to about 70 wt %, about 70 wt % to about 75 wt %, about 75 wt % to about 80 wt %, about 80 wt % to about 85 wt %, about 85 wt % to about 90 wt %, or any other value or range of values therein). In certain embodiments, the aqueous compositions comprise from about 80 wt % to about 90 wt % water or about 90 wt. % to about <100 wt. % water.

The present aqueous compositions can further comprise an organic solvent, in the absence or presence of water in an amount sufficient to keep the extract in solution or to dissolve a dry extract. Suitable organic solvents include, but are not limited to, $C_1$ to $C_4$ alcohols such as methanol, ethanol, n-propanol and i-propanol, n-butanol, sec-butanol, isobutanol and tert-butanol. Alternatively, glycols such as ethylene glycol, propylene glycol and polyethylene glycol, and ketone-containing solvents such as acetone can be employed. In certain embodiments, the aqueous organic solvent is ethanol or i-propanol. In one embodiment, the aqueous compositions comprise water and an alcohol; in another embodiment, water and ethanol or i-propanol. The amount of organic solvent, if present, can be selected based on factors such as its miscibility in water, if present, and the amount of *Eruca sativa* extract. In some embodiments, the organic solvent can be present in the aqueous compositions in an amount ranging from 0 wt % to about 10 wt % (e.g., 0 wt % to about 1 wt %, about 1 wt % to about 2 wt %, about 2 wt % to about 3 wt %, about 3 wt % to about 4 wt %, about 4 wt % to about 5 wt %, about 5 wt % to about 6 wt %, about 6 wt % to about 7 wt %, about 7 wt % to about 8 wt %, about 8 wt % to about 9 wt %, about 9 wt % to about 10 wt %, or any other value or range of values therein) of the aqueous composition. In some embodiments, the aqueous compositions do not comprise an organic solvent.

The aqueous compositions of the invention can further contain one or more other additives. Suitable additives include, but are not limited to, detergents, as surface tension modifiers, flocculants, dispersants, rheology modifiers, emulsifiers, surfactants, chelators, and solvents. Illustrative additives are polysorbates, oils (e.g., canola oil, vegetable oils, etc.). In some embodiments, the additive(s) can be present in the aqueous compositions in amounts ranging from 0 to about 30 wt % (e.g., 0 to about 0.5 wt %, about 0.5 wt % to about 1 wt %, about 1 wt % to about 2 wt %, about 2 wt % to about 3 wt %, about 3 wt % to about 4 wt %, about 4 wt % to about 5 wt %, about 5 wt % to about 6 wt %, about 6 wt % to about 7 wt %, about 7 wt % to about 8 wt %, about 8 wt % to about 9 wt %, about 9 wt % to about 10 wt %, about 10 wt % to about 11 wt %, about 11 wt % to about 12 wt %, about 12 wt % to about 13 wt %, about 13 wt % to about 14 wt %, about 14 wt % to about 15 wt %, about 15 wt % to about 16 wt %, about 16 wt % to about 17 wt %, about 17 wt % to about 18 wt %, about 18 wt % to about 19 wt %, about 19 wt % to about 20 wt %, about 20 wt % to about 21 wt %, about 21 wt % to about 22 wt %, about 22 wt % to about 23 wt %, about 23 wt % to about 24 wt %, about 24 wt % to about 25 wt %, about 25 wt % to about 26 wt %, about 26 wt % to about 27 wt %, about 27 wt % to about 28 wt %, about 28 wt % to about 29 wt %, about 29 wt % to about 30 wt %, or any other value or range of values therein) of the aqueous composition.

In some embodiments, the present aqueous compositions will contain a surfactant. Surfactants are compounds that lower the surface tension of a liquid, the interfacial tension between two liquids, or that between a liquid and a solid. Surfactants may act as detergents, wetting agents, emulsifiers, foaming agents, and dispersants. Surfactants that can be present in the compositions of the invention include anionic surfactants, amphoteric surfactants, cationic surfactants, zwitterionic surfactants, non-ionic surfactants, and combinations thereof. Surfactants suitable for use in the present invention can include polysorbates such as polysorbate 20, polysorbate 40, polysorbate 60 or polysorbate 80. An amount of surfactant that is sufficient to emulsify other ingredients in an aqueous composition or that is sufficient to lower surface tension of a pharmaceutical composition so as to maximize contact between a wound and the *Eruca sativa* extract or maximize antimicrobial activity may be selected.

Serums. A serum refers to a light, quickly absorbed composition that exposes and permits rapid uptake of an active ingredient by skin. It can be used as an alternative to heavier creams or lotions that contain occlusive, or airtight, moisturizing ingredients such as petrolatum or mineral oil that keep water from evaporating. Serums usually contain fewer lubricating and thickening agents, like nut or seed oils, than creams or lotions. Most serums are water-based or based on hydrophilic components, eliminating oils altogether. A serum may be formulated to contain a higher concentration of an active ingredient, such as *Eruca sativa* extract, than a cream or lotion.

Gels. Gels provided herein include semi-solid suspensions that contain an *Eruca sativa* extract. The gels can be single- or two-phase systems. The gels can be oil or liquid based. Single-phase gels can contain small organic macromolecules distributed substantially uniformly throughout a liquid, such that the there is no boundary between the macromolecules and liquid. The liquid can be aqueous, but also contain an alcohol, and, optionally, an oil. Single-phase gels can be made from synthetic macromolecules or from natural gums. Two-phase gels can include a network of small, discrete particles. In one embodiment, two-phase gels are thixotropic. In one embodiment, the organic macromolecules include crosslinked acrylic acid polymers such as the "carbomer" family of polymers (i.e., carboxypolyalkylenes). The organic macromolecules can also be hydrophilic polymers such as polyethylene oxides, polyoxyethylene-polyoxypropylene copolymers and polyvinyl alcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum, sodium alginate; and gelatin. In another embodiment, the organic macromolecules having a stabilizing action include long-chain linear high molecular weight polysaccharides with a molecular weight of more than one million. In this embodiment, 0.1 to 1.5 wt % of such stabilizers are included. In another embodiment, a uniform gel can be prepared by adding dispersing agents such as alcohol or glycerin. In another embodiment, the organic macromolecules can be dispersed by trituration, mechanical mixing or stirring, or combinations thereof. In another embodiment, the liquid can be either water or all water-miscible solvents. Examples of applicable solvents include alkanols, such as ethanol and isopropyl alcohol, benzyl alcohol, propylene glycol and similar solvents.

Creams/Emulsions. Creams provided herein include liquids or semi-solid emulsions with a viscous consistency. Creams can be either oil-in-water or water-in-oil based formulations. Cream bases can be water soluble. Cream bases can contain the following components: (1) an oil phase, (2) an aqueous phase, and (3) an emulsifier. The oil phase can comprise petroleum jelly and a fatty alcohol, such as cetyl or stearyl alcohol. The aqueous phase can contain a humectant. The emulsifier can be a nonionic, anionic, cationic or amphoteric surfactant. In one embodiment, the oil phase includes, but is not limited to, cetyl alcohol, stearyl alcohol, stearic acid, liquid paraffin, and dimethicone. In another embodiment, the water phase ingredient includes, but is not limited to, glycerol and ethyl paraben as well as *Eruca sativa* aqueous extract. In another embodiment, the emulsifying agent includes, but is not limited to, fatty alcohol polyoxyethylene ether (Peregal A-20), polyoxylstearate (SG-6), or combinations thereof.

Lotions. Lotions provided herein include liquids or semi-liquid formulations that are generally lower in viscosity than a cream or gel. The lotions can be an oil-in-water formulation stabilized by a surface-active agent and are usually suitable for application to unbroken skin.

In one embodiment, the lotions contain suspending agents to produce better dispersions and compounds useful for localizing and holding the active agent such as components of an *Eruca sativa* aqueous extract in contact with the skin, including methylcellulose, sodium carboxymethyl-cellulose, and similar compounds.

Ointments. Ointments provided herein include semi-solid preparations that have petroleum jelly or their derivatives as a base. Petroleum jelly is a semi-solid mixture of hydrocarbons. As described in *Remington: The Science and Practice of Pharmacy,* 19th Ed. (Easton, Pa.: Mack Publishing Co., 1995), at pages 1399-1404, ointment bases can be grouped in four classes: oleaginous bases; emulsifiable bases; emulsion bases; and water-soluble bases. Oleaginous ointment bases include vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin, and hydrophilic petroleum jelly. Emulsion ointment bases are either water-in-oil or oil-in-water emulsions, and include, for example, cetyl alcohol, glyceryl monostearate, lanolin, and stearic acid. An ointment may contain solid or encapsulated particles of a dry *Eruca sativa* aqueous extract or may contain an emulsified or suspended *Eruca sativa* aqueous extract.

Pastes. Pastes included herein contain, in addition to an ointment or cream base, high amounts of pulverulent constituents, such as zinc oxide, talc, starch or titanium dioxide.

In one embodiment, the paste is selected from the group comprising fatty pastes or single-phase aqueous gels. The fatty paste includes petroleum jelly, hydrophilic petroleum jelly, or other similar compounds. The single-phase aqueous gel can incorporate carboxymethylcellulose or similar compounds. A paste may contain solid or encapsulated particles of a dry *Eruca sativa* aqueous extract or may contain an emulsified or suspended *Eruca sativa* aqueous extract.

Aerosols. Aerosol as provided herein includes products packaged under pressure and contain ingredients that are released upon activation of an appropriate valve system. Aerosols include all self-contained pressurized products, such as fine mists of spray or foam, that are emitted from a pressurized container containing a propellant, foams, or semisolid liquids. They may also be emitted by an unpressurized atomizer that is pressurized by a hand-operated pump rather than by stored propellant. In one embodiment, the aerosol comprises a container, a propellant, a concentrate containing an active ingredient, a valve (which may be a metered valve), and an actuator. The nature of these components determines characteristics such as delivery rate, foam density, and fluid viscosity. In another embodiment, the aerosol is a two-phase formulation comprising a gas and liquid. In another embodiment, the aerosol is a three-phase formulation comprising a gas, liquid, and suspension or emulsion of active ingredients. In this formulation, suitable excipients, such as wetting agents and/or solid carriers such as talc or colloidal silicas are included. In another embodiment, the propellant is liquefied or vaporized. In another embodiment, a solvent can be the propellant or a mixture of the propellant and co-solvents such as alcohol and polyethylene glycols. In another embodiment, the propellant is selected from the group comprising a spray, foam, or quick-breaking foam. In another embodiment, spray formulations are aqueous solutions in a container having a spray means, such as an atomizer or nebulizer. A spray may contain an aerosol of solid or encapsulated particles of a dry *Eruca sativa* aqueous extract composition or may contain an *Eruca sativa* aqueous extract in an atomized or aerosol liquid form.

Foams. In some embodiments, an *Eruca sativa* aqueous extract is delivered to the body while in a foam state, such as stable foam, for example, that is produced with or without a propellant. For example, the extract may be contained in a shaving foam and used for preventing bacterial infection of nicks, cuts or abrasions associated with shaving. In some versions, a foam is dispensed from a dispenser such as a propellant-free dispenser with pumping action to create the foam from a composition in a foamable carrier, and then applied to a wipe or other substrate, or applied to the hand of the user or otherwise delivered to the skin. Propellant-driving foam generators may also be used to deliver the composition in the form of a foam. Active ingredients in a foam may be dispensed for subsequent placement on a dry wipe, a pre-moistened wipe, or other soft, flexible applicator (e.g., an object about 3-fingers wide or 4 to 10 cm wide) or other object to be used for application of the foam-based composition to the skin. The foam can be a non-propellant foam. A foam with a suitable stiffness of yield stress can be applied to the skin in any manner for sustained adherence and contact with the body. Examples of foam-based systems are described in U.S. Pat. No. 6,818,204, "Stable Foam for Use in Disposable Wipe," issued to Lapidus on Nov. 16, 2004, herein incorporated by reference. The Lapidus patent involves the use of compatible surfactants, e.g., nonionic, anionic, amphoteric, for use in human hygienic products. The surfactant should be capable of forming a foam when mixed with air in a finger actuated, mechanical pump foamer. Such surfactants are said to include, without limitation, those which do not irritate mucous membranes such as polyethylene 20 cetyl ether (Brij 58).™, a nonionic surfactant; sodium lauroyl sarcosinate (Hamposyl L-30).™, sodium lauryl sulfoacetate (Lathanol LAL)™. and sodium laureth sulfate (Sipon ESY)™, anionic surfactants; lauramidopropyl betaine (Monateric LMAB™), an amphoteric surfactant, as well as polysorbate 20, TEA-cocoyl glutamate, disodium cocoamphodiacetate and combinations thereof. Typically, the surfactant is said to present in an amount from about 2% to about 35% by weight, or from about 5% to about 15% by weight.

At least one foam stabilizing agent may be present in some foamable embodiments. Suitable foam stabilizing agents may include, without limitation, natural or synthetic gums such as xanthan gum, polyalkylene glycols such as polyethylene glycol, alkylene polyols such as glycerine and propylene glycol and combinations thereof. Typically, the foam stabilizers may be present in an amount from about 0.10% to about 5%, or from about 2% to about 4%. In the Lapidus patent (U.S. Pat. No. 6,818,204), alkylene polyols are said to be typically employed in amounts from about 0.1% to about 10%, gums are employed in amounts ranging from about 0.05% to about 1%, and/or polyalkylene glycols are present in amounts ranging from about 0.05% to about 2%.

A foam may be produced using the F2 Finger Pump Foamer™. manufactured by AirSpray International Inc. of Pompano Beach, Fla. Such a spring-loaded valve system operates without the use of gas propellants or the like. Upon actuation, precise amounts of air and liquid are mixed, and a foam capable of maintaining its structure for a substantial length of time is dispensed. In addition, the dispenser can deliver a variable amount of foam, thereby reducing waste of the wipe agent contained therein. Details of exemplary propellantless defoamers are described in U.S. Pat. No. 5,443,569, issued on Aug. 22, 1995, and U.S. Pat. No. 5,813,576, issued Sep. 29, 1998, herein incorporated by reference.

Other ingredients in topical formulations. The topical formulations provided herein can include additional ingredients to affect the physical or functional characteristics of the formulations. Stabilizers, preservatives, humectants, regreasing agents, solvents or auxiliaries can be included to improve efficacy and dermal penetration. Dermal penetration-enhancing compounds provided have low toxicity to the skin and can promote percutaneous and oral mucosal absorption. In one embodiment, dermal penetration-enhancing compounds include propylene glycol, polyethylene glycol, dimethylsulphoxide, decylmethylsulphoxide, azones, N-methylpyrrolidone, diethyltoluamide, ethanol, isopropyl myristate, isopropyl palmitate, oleic acid and its esters, medium-chain triglycerides, dimethyl isosorbitol, 2-octyl-dodecanol, branched fatty acids, benzyl alcohol, urea, salicylates and surfactants. Viscosity enhancers or thickeners can be included. Such enhancers can prevent the formulation from spreading beyond the site of application. In one embodiment, Balsam Fir is a pharmaceutically acceptable viscosity enhancer. Another benefit of increasing the viscosity of the formulation is provided below in the section discussing thixotropic agents. Thickeners include suitable polymers such as carbomer, hydroxypropyl methylcellulose, hydroxyethylcellulose, PVM/MA decadiene cross-polymer and acrylates. Two or more thickeners can be added.

Spreading oils or emollients can be included. One benefit for including such oils is for better distribution on surfaces, in particular on the skin. Spreading oils are understood as those oily liquids which are distributed particularly easily on the skin. They are known as such in cosmetics. The following compounds are suitable spreading agents: silicone oil, fatty acid esters, such as ethyl stearate, di-n-butyl adipate, hexyl laurate and dipropylene glycol pelargonate, esters of a branched fatty acid of medium chain length with saturated $C_{16}$-$C_{18}$ fatty alcohols, isopropyl myristate, isopropyl palmitate, caprylic/capric acid esters of saturated fatty alcohols of $C_1$-$C_{18}$ chain length, isopropyl stearate, oleyl oleate, decyl oleate, ethyl oleate, ethyl lactate, waxy fatty acid esters, such as synthetic duck uropygial gland fat, dibutyl phthalate, diisopropyl adipate, ester mixtures related to the latter and the like. Other elements that can be included are emollients, such diisopropyl adipate/isohexadecane dimethicone, occlusive agents, such as example cyclomethicone, trimethylsiloxysilicate, glycereth-26 or polyquaternium-7, emulsifiers, such as cetyl alcohol, stearyl, stearic acid, glyceryl stearate, propylene glycol isostearoyl-sodium isostearoyl, a lactylate, polyoxyethylene (100) stearate, skin conditioners, moisturizers, humectants, such as propylene glycol or glycerin, preservatives, such as phenoxyethanol and parabens, pH adjusting agents, surfactants, chelators, such as disodium EDTA or sodium citrate, tackifying agents, fragrances and other compounds.

Other compounds that can be included in the topical formulation include other antimicrobial, antibacterial, anti-inflammatory ingredients, or other functional ingredients such as protectants from UV. These include, but not limited to, antibiotics that target Gram-negative or Gram-positive bacterial, antifungal compounds, NSAIDS, glucocorticoids (e.g., hydrocortisone and derivatives having the same core ring structure), benzyl alcohol, other botanical extracts or oils, such as those described herein.

The compositions of this invention may be used in conjunction with other active ingredients, such as phyto-chemicals or non-*Eruca sativa* extracts, bacteriostatic agents, bactericidal agents, antibiotics, antiseptics, or anti-inflammatory agents.

Encapsulation. The *Eruca sativa* extracts described herein can be encapsulated in a carrier such as in liposomes, micelles, or microspheres. Suitable carriers are described in U.S. Pat. No. 7,205,003, hereby incorporated by reference.

Micelles. Micelles provided herein can comprise surfactant molecules arranged such that their polar head groups form an outer spherical shell, while their hydrophobic, hydrocarbon chains are oriented towards the center of the sphere, forming a core. The precursor and agent are encapsulated within the core of the micelle. Surfactants suitable for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylanmonium bromide, tetradecyltrimethyl-ammonium bromide, tetradecyltrimethyl-ammonium chloride, dodecylammonium chloride, polyoxyl-8 dodecyl ether, polyoxyl-12 dodecyl ether, nonoxynol 10, and nonoxynol 30.

Liposomes. Liposomes provided herein are microscopic vesicles having a lipid wall comprising a lipid bilayer. Liposomal preparations herein include cationic (positively charged), anionic (negatively charged), and neutral preparations. Cationic liposomes include N[1-2,3-dioleyloxy)pro-pyl]-N,N,N-triethylammonium (DOTMA). Anionic and neutral liposomes can be easily prepared using materials such as phosphatidyl choline, cholesterol, phosphatidyl ethanolamine, dioleoylphosphatidyl choline (DOPC), dio-leoylphosphatidyl glycerol (DOPG), and dioleoylphoshatidyl ethanolamine (DOPE). These materials can also be mixed with DOTMA in appropriate ratios.

Microsphere. Microspheres provided herein can comprise micro- or nano-scale carriers that are made of polymers, both synthetic and natural. Additional nomenclature describing microspheres include, but are not limited to, spheres, beads, particles, carriers, microbeads, microparticles, micro-carriers, nanospheres, nanobeads, nanoparticles, and nano-carriers.

Polymeric materials suitable for the microspheres provided herein include those that are described in U.S. Pat. No. 6,423,345, hereby incorporated by reference in its entirety for all purposes, including poly(hydroxy acids) such as poly(lactic acid), poly(glycolic acid), and poly(lactic acid-co-glycolic acid), poly(lactide), poly(glycolide), poly(lactide-co-glycolide), polyanhydrides, polyorthoesters, poly-amides, polycarbonates, polyalkylenes such as polyethylene and polypropylene, polyalkylene glycols such as poly(eth-ylene glycol), polyalkylene oxides such as poly(ethylene oxide), polyalkylene terepthalates such as poly(ethylene terephthalate), polyvinyl alcohols, polyvinyl ethers, polyvi-nyl esters, polyvinyl halides such as poly(vinyl chloride), polyvinylpyrrolidone, polysiloxanes, poly(vinyl alcohols), poly(vinyl acetate), polystyrene, polyurethanes and co-poly-mers thereof, derivativized celluloses such as alkyl cellu-lose, hydroxyalkyl celluloses, cellulose ethers, cellulose esters, nitro celluloses, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt (jointly referred to herein as "synthetic celluloses"), polymers of acrylic acid, meth-acrylic acid or copolymers or derivatives thereof including esters, poly(methyl methacrylate), poly(ethyl methacrylate), poly(butylmethacrylate), poly(isobutyl methacrylate), poly (hexylmethacrylate), poly(isodecyl methacrylate), poly(lau-ryl methacrylate), poly(phenyl methacrylate), poly(methyl acrylate), poly(isopropyl acrylate), poly(isobutyl acrylate), and poly(octadecyl acrylate)(jointly referred to herein as "polyacrylic acids"), poly(butyric acid), poly(valeric acid), and poly(lactide-co-caprolactone), copolymers and blends thereof. As used herein, "derivatives" include polymers having substitutions, additions of chemical groups, for example, alkyl, alkylene, hydroxylations, oxidations, and other modifications routinely made by those skilled in the art. Natural polymers including agarose and alginate are also suitable for the microspheres. Any of the above carriers can include proteins, lectins, and other biological materials. The precursors and activating agents can be encapsulated into the carriers using known techniques in the art, including micro-spheres described in U.S. Pat. No. 6,423,345, incorporated by reference, including solvent evaporation, hot melt micro-encapsulation, solvent removal, and spray drying of micro-spheres. In one embodiment, the microsphere comprises a block copolymer. In another embodiment, the microsphere comprises a hydrogel.

Suppositories. In addition to the active *Eruca sativa* extract, a suppository may contain the customary water-soluble or water-insoluble excipients, for example polyeth-ylene glycols, fats, for example cocoa fat and higher esters (e.g., $C_{14}$-alcohol with $C_{16}$-fatty acid) or mixtures of these substances.

Tablets, Capsules, Pills. In some embodiments, the *Eruca sativa* aqueous extract will be formulated as a tablet, capsule or pill that contains an *Eruca sativa* aqueous extract. These may contain the customary excipients, such as fillers and extenders, for example starches, lactose, sucrose, glucose, mannitol, and silicic acid; binders, for example carboxymethyl cellulose, alginates, gelatin, polyvinylpyrrolidone; humectants, for example glycerin; disintegrating agents, for example agar-agar, calcium carbonate and sodium carbonate; dissolution retardants, for example paraffin; resorption accelerating agents, for example quaternary ammonium compounds; wetting agents, for example cetyl alcohol, glycerol monostearate; adsorption agents, for example kaolin and bentonite; and lubricants, for example talcum, calcium stearate and magnesium stearate, and solid polyethylene glycols or mixtures of the substances mentioned above. In some embodiments, the active ingredient(s) can be in a microencapsulated form in the tablet or capsule, which can optionally be formulated to release the active *Eruca sativa* component at a particular location within the GI tract, e.g, to transit the stomach and release the active component in the small or large intestine.

Powder. A composition according to the invention may be formulated in the form of an antimicrobial powder which contains a dry or encapsulated *Eruca sativa* extract and the customary excipients, for example lactose, talcum, silicic acid, aluminum hydroxide, calcium silicate, and polyamide powder, or mixtures of these substances. Such powders may be formulated for topical application or for inhalation.

Deodorant/Personal Care. The compositions of the invention can be formulated as deodorants or personal care products that prevent the formation of body odors such as those produced by the growth of Gram-positive bacteria in or on the skin. Such deodorant will contain an antimicrobial amount of the *Eruca sativa* extract and suitable excipients or carriers to facilitate its application to the body. *Eruca sativa* extract may be incorporated into conventional body washes, lotions, lubricants, personal care composition, antiperspirants, or deodorants. Such products are well known in the art and commercially available and are also described by Broad, U.S. Pat. No. 4,252,789, which is incorporated by reference, especially for their descriptions of conventional deodorant ingredients, formulations, and modes of use. These products can be applied to the axilla, inguinal region, feet or other odor-producing body part to prevent growth of odor-causing microorganisms. In other embodiments, the extract of the invention can be incorporated into a deodorizer, cleaner, or disinfectant such as a liquid sanitizer or disinfectant, a spray or wipe for cleaning surfaces exposed to bacterial contaminants.

Cleaning Agent. A composition containing an *Eruca sativa* aqueous extract may be formulated for use as a cleaning or disinfecting agent, such as a hard surface cleaning product. It may further contain cleaning agents, such as chelators or surfactants, which do not interfere with the antimicrobial activity of the *Eruca sativa* extract. The formulation of such a cleaning or disinfecting solution and inclusion of general cleaning agents can easily be done by a skilled artisan and the stability and effectiveness of the solution can be easily tested by the skilled artisan. The term "hard surface cleaning composition" refers to a composition that is used to clean and/or sanitize a hard or solid surface. In one embodiment, the invention provides a composition that prevents bacterial growth on hard surfaces including, but not limited to, surgical instruments, storage tanks, pipelines, trays, containers, walls, floors, countertops, locker room floors, benches, lockers, showers, bathrooms, toilets, water filtration units, and the like.

Foods, Beverages & Feeds. In other embodiments, the formulation is in the form of an ingestible food or beverage or in an additive or protectant in aquaculture. It may be a human food or animal feed that contains an *Eruca sativa* aqueous extract. Such extracts may be incorporated into animal feeds for mammals (cattle, sheep, goats, etc.), birds (e.g., chickens, turkeys, quail, ducks, geese, hawks, falcons, etc.), fish (e.g., tilapia, carp, catfish, salmon, trout, aqua cultured fish, etc.), and crustaceans (e.g., shrimp, lobsters, etc.), mollusks (e.g., abalone, oysters, clams, mussels, etc.). In some embodiments, the *Eruca sativa* extract of the invention will be incorporated into a liquid medium in which an animal is grown, e.g., into a medium for aquaculture. In other embodiments, the extract may be encapsulated in a form that permits uptake by an animal, for example, in an encapsulated particulate form that can be ingested by fish.

Plants. In some embodiments, the *Eruca sativa* extract of the invention can be applied to control the growth of Gram positive bacteria in or on plants, such those causing leaf spots, rots, scabs, and wilting. It may be sprayed or otherwise applied to the roots, foliage, flowers or seeds of a plant. It may be added to culture medium used for hydroponic cultivation of plants.

In many embodiments, the *Eruca* salt aqueous extract will exert antimicrobial activity one anti-Gram positive bacteria. Antimicrobial activity may be determined or quantified by assays known in the art. Representative assays are described below.

Antimicrobial Assays. The term "antimicrobial" when used in the context of an antimicrobial agent or antimicrobial composition, refers to an agent or composition that can kill or otherwise inhibit the growth or proliferation of microbes including, for example, bacteria, viruses and fungi. Similarly, the term "antimicrobial activity" as used herein refers to activity that can kill or otherwise inhibit the growth or proliferation of microbes including bacteria, yeasts, viruses and fungi.

When used as an antimicrobial agent, those skilled in the art understand that it is beneficial to select extraction, treatment, purification, and storage conditions of the *Eruca sativa* aqueous extract to maximize the anti-microbial or therapeutic activity of a composition containing the extract, for example, by selecting an appropriate concentration of the extract. These selections may be made based on the results of the antimicrobial assays described below.

The antimicrobial or antibacterial activity of the *Eruca sativa* extract of the invention may be determined using standard assays and procedures known in the art. A skilled artisan will know how to conduct an assay including the use of appropriate controls, negative and positive, to ensure the results of the assay are meaningful. Common antimicrobial assays include the broth dilution and agar diffusion assays.

In the broth dilution method, the minimum concentration required to inhibit bacterial growth (minimum inhibitory concentration, MIC) is determined using a series of tubes containing serial dilutions of the extract in broth inoculated with a test microorganism.

In the disc diffusion method, paper or porous discs impregnated with a test extract are placed on a semi-solid (agar based) medium which has been uniformly inoculated with a microorganism. After incubation, zones of inhibition of bacterial growth around the discs are measured. Inhibition may be quantified by reference to that caused by control discs containing known concentrations of antimicrobial compounds such as antibiotics. Disc diffusion assays are incorporated by reference to Mohanty A, et al, *Physiochemical and Antimicrobial Study of polyherbal Pharmacieglobal,* 4 (04): 1-3 (2010) or to the Kirby-Bauer method described by hypertext transfer protocol://web.archive.org/web/

20130731092046/ and hypertext transfer protocol://ami-nj.myweb.uga.edu:80/KIRBY-BAUER.html (last accessed Mar. 28, 2017).

Standardization of *Eruca sativa* extract microbial activity. The antimicrobial activity of an aqueous *Eruca sativa* extract may be determined by its effect on a bacterial strain, such the B22 *Cellulomonas uda* reference strain or another *Cellulomonas* strain such as *Cellulomonas* sp. ATCC 21399 described as follows and incorporated by reference to hypertext transfer protocol secure://www.atcc.org/products/all/ 21399.aspx (last accessed Jun. 6, 2017):

*Cellulomonas* sp.

21399™

Description

Strain designation: [NCIB 11494]

Deposited As: *Cellulomonas* sp.

Type strain: No

Patent depository: This material was deposited with the ATCC Patent Depository to fulfill U.S. or international patent requirements. This material may not have been produced or characterized by ATCC. As an International Depository Authority (IDA) for patent deposits, ATCC is required to complete viability testing only at time of initial deposit of patent material. Patent deposits are made available on behalf of the Depositor when the pertinent U.S. or international patent is issued, but material may not be used to infringe the patent claims.

Patent number: 3,627,095—incorporated herein by reference.

Technical information: ATCC Technical Services does not have technical information on patent deposits that are not produced or characterized by ATCC. Additional information can be found in the corresponding patent available from the patent holder or with the U.S. and/or international patent office.

Storage Conditions

Product format: Freeze-dried

Intended Use: This product is intended for laboratory research use only. It is not intended for any animal or human therapeutic use, any human or animal consumption, or any diagnostic use.

BSL 1—ATCC determines the biosafety level of a material based on our risk assessment as guided by the current edition of Biosafety in Microbiological and Biomedical Laboratories (BMBL), U.S. Department of Health and Human Services. It is your responsibility to understand the hazards associated with the material per your organization's policies and procedures as well as any other applicable regulations as enforced by your local or national agencies. ATCC highly recommends that appropriate personal protective equipment is always used when handling vials. For cultures that require storage in liquid nitrogen, it is important to note that some vials may leak when submersed in liquid nitrogen and will slowly fill with liquid nitrogen. Upon thawing, the conversion of the liquid nitrogen back to its gas phase may result in the vial exploding or blowing off its cap with dangerous force creating flying debris. Unless necessary, ATCC recommends that these cultures be stored in the vapor phase of liquid nitrogen rather than submersed in liquid nitrogen.

Growth Conditions

Medium:

ATCC Medium 464: *Cellulomonas* PTYG medium

Temperature: 30° C.

Handling Procedures

1. Open vial according to enclosed instructions.

2. Using a single tube of #464 broth (5 to 6 ml), withdraw approximately 0.5 to 1.0 ml with a Pasteur or 1.0 ml pipette. Rehydrate the entire pellet.

3. Aseptically transfer this aliquot back into the broth tube. Mix well.

4. Use several drops of the suspension to inoculate a #464 agar slant and/or plate.

5. Incubate the tubes and plate at 30° C. for 24 hours.

Notes—Colonies on #464 agar are entire, glistening, circular, smooth, low convex, and opaque, becoming yellowish with age;

or to the other commercially available *Cellulomonas* strains available at the ATCC which are incorporated by reference to the link below last accessed Jun. 6, 2017: hypertext transfer protocol secure://www.atcc.org/ Search_Results.aspx?dsNav=Ntk:PrimarySearch %7c *Cellulomonas*+sp.%7c3%7c, Ny:True,Ro:0,N: 1000552&searchTerms=*Cellulomonas*+sp.&redir=1.

For example, the dried aqueous extracts described in Examples 1-4 can be dissolved in water or in a suitable buffer and applied at a specific concentration to a disc for use in a disc-diffusion assay or serially diluted for use in a broth dilution assay. A liquid *Eruca sativa* extract or a composition containing an *Eruca sativa* aqueous extract may be tested in a similar way and the dry or solid content of such a liquid extract used to standardize comparisons of liquid extracts at different concentrations.

"Gram-positive bacteria" are bacteria that give a positive result in the Gram stain test. Gram-positive bacteria take up the crystal violet stain used in the test, and then appear to be purple-colored when seen through a microscope. This is because the thick peptidoglycan layer in the bacterial cell wall retains the stain after it is washed away from the rest of the sample, in the decolorization stage of the test. In general, the following characteristics are present in gram-positive bacteria (i) a cytoplasmic lipid membrane, (ii) a thick peptidoglycan layer, (iii) teichoic acids and lipoids are present, forming lipoteichoic acids, which serve as chelating agents, and also for certain types of adherence, (iv) peptidoglycan chains that are cross-linked to form rigid cell walls by a bacterial enzyme DD-transpeptidase, (v) a much smaller volume of periplasm than that in gram-negative bacteria.

Representative Gram-positive bacteria include bacilli and cocci. Bacilli include *Corynebacteria, Clostridium, Listeria* and *Bacillus*. Cocci include *Staphylococcus* and *Streptococcus*. Representative species include *Staphylococcus aureus* (including MRSA), *Staphylococcus epidermidis*, and *Staphylococcus saprophyticus*; and *Streptococcus pyogenes, Streptococcus agalactiae. Streptococcus pneumoniae, Streptococcus viridans, Enterococcus faecalis. Enterococcus faecium*. In preferred embodiments, the *Eruca sativa* aqueous extract will exert antimicrobial activity on one or more of the Gram positive bacteria described above, such as *Cellulomonas* strain B22. *Cellulomonas* is a genus of Gram-positive rod-shaped bacteria. One species is *Cellulomonas uda* (incorporated by reference to hypertext transfer protocol:// www.uniprot.org/taxonomy/1714, last accessed Jun. 6, 2017). Other *Cellulomonas* species and their features are incorporated by reference to hypertext transfer protocol:// www.bacterio.net/cellulomonas.html (last accessed Jun. 6, 2017) and to the references cited there. One of their main distinguishing features is their ability to degrade cellulose, using enzymes such as endoglucanase and exoglucanase. They are members of the actinobacteria. Extracts according to the invention may be employed to inhibit growth or activity, such as enzyme activity, of Gram-positive bacteria.

Other Gram-positive bacteria which are plant pathogens include *Burkholderia,* and Proteobacteria such as *Xanthomonas* spp. and *Pseudomonas* spp. The extract of the invention may be used, for example, by application to plant surfaces, to control such plant pathogens.

"Mollicutes" and "*Mycoplasma*" describe bacteria that lack a cell wall around their cell membrane. These include plant pathogens such as Phytoplasma and Spiroplasma. Without a cell wall, they are unaffected by many common antibiotics such as penicillin or other beta-lactam antibiotics that target cell wall synthesis. *Mycoplasma* species that infect humans include *M. amphoriforme, M. buccale, M. faucium, M. fermentans, M. genitalium, M. hominis, M. lipophilum, M. orale, M. penetrans, M. pirum, M. pneumoniae, M. primatum, M. salivarium,* and *M. spermatophilum.* Phylogenetically, mycoplasmas evolved from Gram-positive bacteria which lost their cell walls. They are associated with cancer (e.g, colon cancer, gastric cancer, lung cancer, prostate cancer, and renal cancer) and host cell transformation as well as with infectious and autoimmune diseases including genital infections and sexually transmitted diseases, pelvic inflammatory disease, male infertility, and pneumonia. In some embodiments, the *Eruca sativa* aqueous extract will exert antimicrobial activity on one or more types of *mycoplasma* described above.

"Gram-negative bacteria" are bacteria that give a negative result in the Gram stain test because they do not retain the crystal violet stain used in the Gram staining method of bacterial differentiation. They are characterized by their cell envelopes, which are composed of a thin peptidoglycan cell wall sandwiched between an inner cytoplasmic cell membrane and a bacterial outer membrane. Gram-negative bacteria include the following genuses and species: *Acinetobacter* (e.g., *A. baumannii*), *Chlamydia* (e.g., *C. trachomatis*), *Escherichia* (e.g. *E. coli*), *Haemophilus* (e.g., *H. influenzae*), *Klebsiella* (e.g., *K. pneumoniae*), *Neisseria* (e.g., *N. gonorrhoeae*), *Pseudomonas* (e.g., *P. aeruginosa*), *Salmonella* (e.g., *S. enterica, S. typhi*), and *Yersinia* (e.g., *Y. pestis*). In some embodiments, the *Eruca sativa* aqueous extract will exert no or minimal antimicrobial activity on one or more of the Gram negative bacteria described above.

Embodiments of the invention include, but are not limited to the following.

A composition comprising an aqueous extract of *Eruca sativa* leaves from which solid components of *Eruca sativa* have been removed. In one embodiment the aqueous extract is produced by grinding, pressing, pulverizing, or otherwise disrupting leaves of *Eruca sativa*, mixing the ground, pulverized, pressed or otherwise disrupted leaves with water for a time sufficient to extract water-soluble components, and removing solid components from the mixture of leaves and water, thereby providing the aqueous extract. Solids may be removed by centrifugation, filtration or by other methods known in the art. In one embodiment the mixing is performed at a pH ranging from 6.0 to 8.0 and at a temperature ranging from 25° C. to 80° C.

The aqueous extract from *Eruca sativa* leaves may be concentrated to less than its original volume by removing the aqueous solvent or water. For example, it may be reduced to 99, 95, 90, 80, 70, 60, 50, 40, 30, 20, 10, 5, 4, 3, 2, 1 of its original volume; or 5, 10, 15, 20, 25, 30, 35, 40, 45, 50, 55, 60, 65, 70, 75, 80, 85, 90, 95, 99, or 100 wt % of the water or solvent may be removed. All of the solvent or water may be removed from the aqueous extract to produce an anhydrous or solid aqueous extract. This advantageously provides a way to standardize the solid content of compositions according to the invention and to compare the antimicrobial activity of different aqueous extracts. For example, the amount of the anhydrous extract may be adjusted to a concentration sufficient to inhibit growth of a Gram-positive bacterium, such as *Cellulomonas* strain B22 or other strains such as *Bacillus* sp. B22 (2014) incorporated by reference to hypertext transfer protcol://www.uniprot.org/taxonomy/1529852 (last accessed Jun. 7, 2017).

In another embodiment, an original, concentrated, purified, or solid aqueous extract will be formulated to contain one or more other ingredients such as a carrier, excipient, or support such as those described herein. Nonlimiting examples of such embodiments include those in the form of an aqueous solution, tincture, humectant, absorbent, desiccant, dry gel, or gel; in the form of an oil-in-water or water-in-oil emulsion; in the form of a serum, cream, or a lotion; in the form of a spray or foam; in the form of a bandage, hydrogel patch, compress, dressing, bed linens, tamponade, tampon, gauze, gauze sponge, medical dressing, diaper or wipe. These products may comprise natural or synthetic components, such as woven or non-woven fibers, textiles or elastic components. Fibers can be customary synthetic or semi-synthetic fibers, such as polyesters, polyolefins and rayon, or customary natural fibers, such as cotton. A textile material can comprise fibers of cellulose materials (e.g. cotton), viscose, linen, flax, hemp, jute and other natural fiber materials. It can also comprise fibers of synthetic fibers such as polyesters, polyamides, polyurethanes, polynitrile, ABS, polyolefins (such as polypropylene) as well as copolymeric materials, such as elastomeric materials and thermoelastic polymers (TPEs).

Another embodiment of the invention is a method for inhibiting growth of a Gram-positive bacterium or *mycoplasma* comprising contacting it with an aqueous extract of leaves of *Eruca sativa* (arugula). Generally, this method will be performed using an extract from which is formulated as described herein, for example in the form of an aqueous solution, a gel, tincture, oil-in-water or water-in-oil emulsion, a cream, a lotion, ointment, paste or powder. Growth or viability of Gram-positive bacteria and/or mycobacteria is inhibited by contact with the extract or with a formulation containing the extract. Advantageously, these formulations may contain 0.01, 0.05, 0.1, 0.2, 0.5, 0.75, 1.0, 2.0, 3.0, 4.0, 5.0, 10.0, 15.0, 20.0 or more wt % of the aqueous extract, wherein the wt % of the aqueous extract is based on weight of anhydrous solids in an aqueous extract of *Eruca sativa* leaves. This range includes all intermediate subranges and values. In one embodiment the amount of aqueous *Eruca sativa* extract is at least 0.15 g/ml.

Another embodiment of the invention is a method for treating a wound or injury (including dermatitis or inflammatory conditions some of which are associated with bacterial infection) comprising contacting it with a composition comprising an aqueous extract of leaves of *Eruca sativa*. Generally, this method will be performed using an extract from which is formulated as described herein, for example in the form of an aqueous solution, a gel, tincture, oil-in-water or water-in-oil emulsion, a cream, a lotion, ointment, paste or powder. Healing of the wound or injury or dermatitis or inflammatory condition is promoted by contact with the extract or with a formulation containing the extract. Advantageously, these formulations may contain 0.01, 0.05, 0.1, 0.2, 0.5, 0.75, 1.0, 2.0, 3.0, 4.0, 5.0, 10.0, 15.0, 20.0 or more wt % of the aqueous extract (or any intermediate value or endpoint), wherein the wt % of the aqueous extract is based on weight of anhydrous solids in an aqueous extract of *Eruca sativa* leaves.

This method may be used to treat wounds, such as punctures, lacerations, abrasions, bites (e.g., mosquito or other insect bites), acne, inflammations, or other lesions in or on the skin, hair, nails, or mucous membranes. Such wounds include pressure ulcers, diabetic ulcers (e.g., diabetic foot ulcers), venous ulcers, lower leg ulcer; bedsores, blisters, eschars/scabs, scalds and burns (first, second and third degree burns), chemical burns, thermal burns such as flame burns and flash burns, ultraviolet burns, contact burns, radiation burns, electrical burns, gangrene, skin tears or lacerations, such as those made by knives; abrasions; punctures such as made by nails, needles, wires, and bullets; incisions such as made by knives, nails, sharp glass, razors; amputations; post-operative infections; surgical wounds; spider (including brown recluse bites), scorpion, centipede, tick, fly, mosquito, bites or stings; failing or compromised skin/muscle grafts or flaps.

This method may also be used to treat wounds in other anatomical locations to which the aqueous extract can be applied or administered, for example, to ulcers or lesions in the GI tract.

In other embodiments it may be used to treat damage associated with aging such as wrinkles, dry skin, age spots, sun damage (particularly UV radiation-induced oxidative stress), blemishes, hyperpigmented skin, age spots, increased skin thickness, loss of skin elasticity and collagen content, dry skin, lentigines and melasmas. In such embodiments, the extract or a formulation containing it is generally contacted with the damage skin or tissue.

In another embodiment an *Eruca sativa* extract can be used or applied as an anti-microbial agent, for example, for the control of cellulose degradation by *Cellulomonas uda*. This microorganism causes significant cellulose degradation and disintegration of plant tissue. A water extract of *Eruca sativa* can be used by itself or as a source of antibacterial compounds against *Cellulomonas uda*. Such an extract or extract components may be used in agriculture as natural compounds to control plant pathogenic bacteria and other microorganisms that can cause serious losses in important crops, vegetable and fruit plant. It may also be applied to seeds, grain, fruit, vegetable, or other edible portions of a plant (or to a food in general) to inhibit growth of bacteria, increase shelf life, or improve commercial appearance of a food product. Furthermore, these naturally sourced extracts can be used to partially or fully replace synthetic pesticides (including bacteriocidal and bacteriostatic agents) and reduce or eliminate the toxic and other negative effects of synthetic agents. Such extracts in liquid or solid form may be applied by means known in the art including by sprayers or dusters.

The following examples further describe and demonstrate embodiments within the scope of the present invention. The examples are given solely for the purpose of illustration and are not to be construed as limitations of the invention. Many variations thereof are possible without departing from the spirit and scope of the present invention.

Example 1

Preparation of *Eruca sativa* Plant Extract

Extraction is the crucial first step in the analysis of medicinal plants, because it is necessary to extract the desired chemical components from the plant materials for further separation and characterization. The basic operation generally includes pre-washing, drying of plant materials, or freeze drying, grinding to obtain a homogenous sample and improve the kinetics of analytic extraction.

Air-dried *Eruca sativa* leaves were ground to a fine powder using a grinder and the resulted material (100 g) was extracted by maceration into 600 ml of water at room temperature with occasional shaking.

After three days, the extract was filtered (45 mm) and was concentrated under vacuum to produce a thick concentrated extract.

The concentrated extract was weighed and preserved in airtight bottles at 4° C. until further use. The resulted residue (22 g) was suspended in 100 ml of distilled water. These fractions were kept at 4° C. in the dark until use or further analysis.

Example 2

Preparation of Cold Water Aqueous Extract of *Eruca sativa* Leaves 100 grams of dried, powdered *Eruca sativa* leaves are suspended in 1 liter of water at room temperature (25° C.) and stirred mechanically for 12 hours. Solids are removed by centrifugation (4,000 g, 10 mins) and the supernatant is collected. The resulting aqueous extract is completely dried in a rotary evaporator at 40° C. and the lyophilized extract is stored at 4° C.

Example 3

Preparation of hot water aqueous extract of *Eruca sativa* leaves 100 grams of dried, powdered *Eruca sativa* leaves are suspended in 1 liter of water at room temperature (80° C.) and stirred mechanically for 1 hour. Solids are removed by centrifugation (4,000 g, 10 mins) and the supernatant is collected. The resulting aqueous extract is completely dried in a rotary evaporator at 40° C. and the lyophilized extract is stored at 4° C.

Example 4

Preparation of a Filtered Cold Water Aqueous Extract of *Eruca sativa* Leaves 100 gr of dried *Eruca sativa* leaves are mashed by pressing and mixed with 1,000 ml of cold water for 12 hours at 25° C. Undissolved components are removed from the resulting suspension by centrifugation (4,000 g, 10 mins) and then from the supernatant by filtration through a 0.45 micron filter. The resulting aqueous extract is completely dried in a rotary evaporator at 40° C. and the lyophilized extract is stored at 4° C.

Example 5

Preparation of a Filtered Hot Water Aqueous Extract of *Eruca sativa* Leaves 100 gr of dried *Eruca sativa* leaves are mashed by pressing and mixed with 1,000 ml of water and mechanically stirred in boiling water for 30 mins at 80° C. Undissolved components are removed from the resulting suspension by centrifugation (4,000 g, 10 mins) and then f-om the supernatant by filtration through a 0.45 micron filter. The resulting aqueous extract is completely dried in a rotary evaporator at 40° C. and the lyophilized extract is stored at 4° C.

Example 6

Assessment in Liquid Culture of Antimicrobial Activity of Aqueous Extract of *Eruca Sativa* Leaves Water extracts of *Eruca sativa* as described in Examples 1-5 are contacted with Gram-positive and Gram-negative bacteria. The effect of *Eruca sativa* water extracts on the growth of Gram-positive test strain B22 is determined by measuring the optical density (OD) of treated and untreated bacterium and counting the number of viable cells (cfu/mL). Tested bacteria include those described below as well as Gram-negative strains.

| Bacteria | Effect |
| --- | --- |
| *Rhodococcus* sp | a plant pathogen, causes leafy gall disease in both angiosperm and gymnosperm plants |
| *Gordonia sputi* | emerging human pathogen that causes a variety of infections in both immunocompromised and immunocompetent hosts, Cutaneous and respiratory infections, otitis externa, osteitis, and arthritis have reportedly occurred only in immunocompetent patients. |
| *Cellulomonas uda* | cellulose degradation and disintegration of plant tissue |
| *Bacillus altitudinis* | soft rot on apple and pear fruits |

Minimum inhibitory concentrations (MIC) of the extract of Example 1 were determined according to Eloff (1998) in sterile 96-well microplates with a final volume of 100 ml in each microplate well. A stock solution of the water extract (250 mg/ml) was prepared. Thereafter, a two-fold serial dilution of the extract was prepared in the microplate wells over the range 0.02-0.25 mg/ml. To each test well, 5 ml of cell suspension was added to reach a final inoculum concentration of $10^5$ cfu/ml. The plates were then covered with sterile plate covers and incubated at 30 C for 48 h. The MIC was defined as the lowest concentration of the extract at which the microorganism does not demonstrate visible growth after incubation. The lowest concentration that yielded no growth after this sub-culturing was taken as the MBC, indicating that >99.9% of the original inoculum was killed. The determination of MIC and MBC values was properly replicated three times.

Antimicrobial activities of the *Eruca sativa* extract were evaluated by means of agar-well diffusion assay according to the method of Andrews (2005) with minor modifications. Fifteen milliliters of the molten agar (45° C.) were poured into sterile petri dishes (Ø 90 mm). Cell suspensions were prepared and 100 ml was inoculated onto the surface of agar plates. Thereafter, wells with 6 mm in diameter were punched in the inoculated agar medium with sterilized Pasteur pipettes and the extracts were added to each well. Negative controls consisting of organic solvent were used to dissolve the plant extracts. The plate was allowed to stand for 2 h at 4° C. to permit the diffusion of the extracts followed by incubation at 30° C. for 48 h. The antibacterial activity was evaluated by measuring the zones of inhibition (clear zone around the well) against the tested microorganisms. All tests were repeated three times.

In this assay, only Gram-positive bacteria were susceptible to the extract and the Gram-negative bacteria were not inhibited at the same concentrations.

Different concentrations of the water extracts are added to different samples of culture media. The results of these experiment show that aqueous extracts of *Eruca sativa* leaves inhibited the growth of B22 strain at 0.15 g/mL (dry weight of extract/volume).

While not being bound to any particular explanation, this resistance is attributed to differences in cell wall structure between Gram-positive and Gram-negative bacteria. Gram-negative bacteria have a permeability barrier comprised of a thin lipopolysaccharide exterior membrane which could restrict the penetration of the extruding the plant extract. In contrast, Gram-positive bacteria have a mesh-like peptidoglycan layer which may be more accessible to permeation by the *Eruca sativa* extract.

Example 7

Assessment on Agar Plates of Antimicrobial Activity of Aqueous Extract of *Eruca Sativa* Leaves Gram-positive or Gram-negative bacteria are plated on to agar plates containing a medium supporting their growth. Thin permeable wafers/discs are infused with control solution (water) or with various concentrations of aqueous extracts of *Eruca sativa* as described in Examples 1-5. Plates with wafers/discs are incubated at 37° C. overnight. The growth of Gram-positive bacteria is inhibited by the *Eruca sativa* leaf extracts at a concentration of 0.15 g/mL (dry weight of extract/volume) as shown by the appearance of a zone of inhibition where growth of Gram positive bacteria is not observed. In contrast, the zone of inhibition for Gram negative bacteria is while the growth of Gram-negative bacteria at the same concentrations is not substantially inhibited as shown by the absence of, or substantially smaller zones of inhibition.

Terminology used in this disclosure is for the purpose of describing particular embodiments only and is not intended to be limiting of the invention. For example, as used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. For example, the term "comprising" will be understood to imply the inclusion of any stated elements or steps but not the exclusion of any other elements or steps. Likewise, the terms "include", "includes" and "including", unless the context requires otherwise, do not exclude unrecited elements or steps.

As used herein, the term "and/or" includes any and all combinations of one or more of the associated listed items and may be abbreviated as "/".

Links are disabled by insertion of a space or underlined space before "www" and may be reactivated by removal of the space.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all subranges and values subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of different embodiments. Combinations of the above embodiments, and other embodiments not specifically described herein, will be apparent to those of skill in the art upon reviewing the above description.

All publications and patent applications mentioned in this specification are herein incorporated by reference in their entirety to the same extent as if each individual publication or patent application is specifically and individually indicated to be incorporated by reference, especially referenced is disclosure appearing in the same sentence, paragraph, page or section of the specification in which the incorporation by reference appears. However, no admission is made with regard to the accuracy of the reference teachings or that these references are applicable prior art.

The invention claimed is:

1. A foam treatment method for killing or inhibiting the growth of a Gram positive bacterium while preventing desiccation of a wound, comprising:
   preparing a disinfectant foam by:
      grinding a sample consisting of dried leaves of a *Eruca sativa* plant,
      macerating the ground leaves of the *Eruca sativa* plant with an extractant consisting of water to extract the leaves of the *Eruca sativa* plant for a period of days at a temperature of about 25° C. to extract water-soluble components from the leaves of the *Eruca sativa* plant then filtering to form a first extract,
      concentrating the first extract under vacuum to produce an aqueous *Eruca sativa* extract in the form of a concentrated extract liquid,
      dispensing a mixture of the concentrated extract and a polysorbate surfactant from a dispenser in the form of the disinfectant foam,
   contacting the Gram positive bacterium with the disinfectant foam to inhibit the growth of the Gram positive bacterium while preventing desiccation of the wound, wherein the disinfectant foam inhibits the growth of or kills *Cellulomonas* strain B22.

2. The foam treatment method of claim 1, wherein the disinfectant foam comprises 5to 15% by weight of the polysorbate surfactant.

3. The foam treatment method of claim 1, wherein said contacting the Gram positive bacterium with the disinfectant foam inhibits the growth of the *Cellulomonas* strain B22 while preventing desiccation of the wound.

4. The foam treatment method of claim 1, wherein the dispensing includes contacting the wound with at least one of a bandage, a hydrogel patch, a compress, or a dressing.

5. The foam treatment method of claim 1, wherein the wound comprises a puncture, laceration, abrasion, or bite.

6. The foam treatment method of claim 1, wherein the wound comprises a burn.

7. The foam treatment method of claim 1, wherein said disinfectant foam comprises no more than 0.5 wt. % of the aqueous extract as measured after removal of water.

* * * * *